(12) United States Patent
Kadayam Viswanathan et al.

(10) Patent No.: US 9,720,124 B2
(45) Date of Patent: Aug. 1, 2017

(54) LOGGING IN GAS SHALE AND OTHER UNCONVENTIONAL RESERVOIRS

(75) Inventors: Ravinath Kausik Kadayam Viswanathan, Boston, MA (US); Chanh Cao Minh, Katy, TX (US); Ridvan Akkurt, Lexington, MA (US); Baarinadh Vissapragada, Walpole, MA (US); Yi-Qiao Song, Newton Center, MA (US); Lukasz Zielinski, Cambridge (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 646 days.

(21) Appl. No.: 14/119,708

(22) PCT Filed: Aug. 9, 2012

(86) PCT No.: PCT/US2012/050058
§ 371 (c)(1),
(2), (4) Date: Feb. 24, 2014

(87) PCT Pub. No.: WO2013/023011
PCT Pub. Date: Feb. 14, 2013

(65) Prior Publication Data
US 2015/0219782 A1 Aug. 6, 2015

Related U.S. Application Data

(60) Provisional application No. 61/521,860, filed on Aug. 10, 2011.

(51) Int. Cl.
*G01V 3/14* (2006.01)
*G01V 3/32* (2006.01)
(Continued)

(52) U.S. Cl.
CPC ............. *G01V 3/14* (2013.01); *G01N 24/081* (2013.01); *G01V 3/32* (2013.01); *G01V 3/38* (2013.01);
(Continued)

(58) Field of Classification Search
CPC ... G01V 3/14; G01V 3/32; G01V 3/38; G01N 24/081; G01R 33/448; G01R 33/56341
See application file for complete search history.

(56) References Cited

U.S. PATENT DOCUMENTS 6,225,803 B1 * 5/2001 Chen .................... G01N 24/081
324/300
6,369,567 B1 4/2002 Song et al.
(Continued)

FOREIGN PATENT DOCUMENTS

WO 9612976 5/1996

OTHER PUBLICATIONS

Akkurt et al., "NMR Logging of Natural Gas Reservoirs," The Log Analyst, Nov.-Dec. 1996: pp. 33-42.
(Continued)

*Primary Examiner* — Rodney Bonnette

(57) ABSTRACT

Apparatus and methods for characterizing hydrocarbons in a subterranean formation include obtaining a sample of the subterranean formation; measuring, uphole, the porosity of the sample; using a nuclear magnetic resonance (NMR) tool downhole in the borehole, sending NMR pulse sequences configured for formation pore size and measuring NMR signals that characterize the formation at a location in the formation; analyzing the signals to find a gas porosity of the formation at the location; and determining a hydrogen index ($HI_g$) of the subterranean formation from the gas porosity and from the porosity of the sample. The obtained $HI_g$ may then be used in conjunction with downhole NMR measurements to find corrected gas porosities at locations of the formation.

19 Claims, 12 Drawing Sheets

| GAS SHALE SAMPLE | CLAY VOLUME (%) | CARBONATE VOLUME (%) | SURFACE TO VOLUME RATIO (*10⁶ M⁻¹) | TOC (%) |
|---|---|---|---|---|
| SAMPLE # 1 | 10 | 74 | 208 | 0.9 |
| SAMPLE # 2 | 40 | 19 | 433 | 4.1 |
| SAMPLE # 3 | 45 | 12 | 425 | 3.2 |
| SAMPLE # 4 | 35 | 32 | 477 | 2.6 |

(51) Int. Cl.
*G01V 3/38* (2006.01)
*G01N 24/08* (2006.01)
*G01R 33/44* (2006.01)
*G01R 33/563* (2006.01)

(52) U.S. Cl.
CPC ...... *G01R 33/448* (2013.01); *G01R 33/56341* (2013.01)

(56) References Cited

U.S. PATENT DOCUMENTS

| | | | |
|---|---|---|---|
| 7,893,692 | B2 | 2/2011 | Minh |
| 2003/0231017 | A1* | 12/2003 | Kiesl .................. E21B 33/1243 324/303 |
| 2005/0264285 | A1* | 12/2005 | Chen ........................ G01V 3/32 324/303 |
| 2006/0097722 | A1 | 5/2006 | Scheven |
| 2006/0272812 | A1* | 12/2006 | Yu ........................ G01N 24/081 166/252.5 |
| 2013/0270011 | A1 | 10/2013 | Akkurt et al. |

OTHER PUBLICATIONS

Ambrose et al., "SPE 131772: New Pore-Scale Considerations for Shale Gas in Place Calculations," SPE International, 2010: pp. 1-17.
Gerritsma et al., "Proton-Spin-Lattice Relaxation and Self-Diffusion in Methanes: II. Experimental Results for Proton-Spin-Lattice Relaxation Times," Physica, 1971, vol. 51: pp. 381-394.
Gordon, "Kinetic Theory of Nuclear Spin Relaxation in Gases," The Journal of Chemical Physics, Jan. 1966, vol. 44(1): pp. 228-234.
Hook et al., "SPE 146883: Improved Precision Magnetic Resonance Acquisition: Application to Shale Evaluation," SPE International, 2011: pp. 1-8.
Hubbard, "Theory of Nuclear Magnetic Relaxation by Spin-Rotational Interactions in Liquids," Physical Review, Aug. 1963, vol. 131(3): pp. 1155-1165.
Kausik et al., "SPE 147198: Characterization of Gas Dynamics in Kerogen Nanopores by NMR," SPE International, 2011: pp. 1-16.
Loucks et al., "Morphology, Genesis and Distribution of Nanometer-Scale Pores in Siliceous Mudstones of the Mississippian Barnett Shale," Journal of Sedimentary Research, 2009, vol. 79: pp. 846-861.
Mattea et al., "Molecular exchange dynamics in partially filled microscale and nanoscale pores of silica glasses studied by field-cycling nuclear magnetic resonance relaxometry," Journal of Chemical Physics, Dec. 2004, vol. 121(21): pp. 10648-10656.
Mitra et al., "Short-time behavior of the diffusion coefficient as a geometrical probe of porous media," Physical Review B, Apr. 1993-II, vol. 47(14): pp. 8565-8574.
Sigal et al., "Laboratory NMR Measurements on Methane Saturated Barnett Shale Samples," Petrophysics, Feb. 2011 (Dec. 2010), vol. 52(1): pp. 32-49.
Zielinski et al., "SPE 134841: Restricted Diffusion Effects in Saturation Estimates from 2D Diffusion-Relaxation NMR Maps," SPE International, 2010: pp. 1-8.

* cited by examiner

LOGGING IN GAS SHALE AND OTHER UNCONVENTIONAL RESERVOIRS

CROSS-REFERENCE TO RELATED APPLICATIONS

This application is a United States National Stage Application under 35 U.S.C. §371 and claims priority to Patent Cooperation Treaty Application Number PCT/US2012/050058 filed Aug. 9, 2012, which claims the benefit of U.S. Provisional Patent Application Ser. No. 61/521,860 filed Aug. 10, 2011. Both of these applications are incorporated herein by reference in their entireties.

BACKGROUND

The nuclear magnetic resonance (NMR) response of gas in gas shale nanopores is different from that of bulk gas, where relaxation is dominated by spin rotation and diffusion is unrestricted. Gas shales are characterized by very low porosity and ultra low permeabilities. Their porosity is dominated by nanometer-scale pores in the organic kerogen that restricts diffusion motion, in addition to having very high surface-to-volume ratios that enhance surface relaxation. At high pressure, the gas exists as an adsorbed phase on the pore surface and as free gas phase in the pore interior. Thus, relaxation and diffusion properties of gas in gas shales are affected by the combined effects of adsorption, enhanced surface relaxation, restricted diffusion and molecular exchange between the adsorbed and free phases.

SUMMARY

Embodiments herein relate to an apparatus and methods for characterizing hydrocarbons in a subterranean formation including sending and measuring NMR signals; analyzing the signals to form a distribution; and estimating a property of a formation from the distribution, wherein the sending comprises pulse sequences configured for a formation pore size, and wherein the computing comprises porosity. Embodiments herein relate to an apparatus and methods for characterizing hydrocarbons in a subterranean formation including sending and measuring NMR signals; analyzing the signals to form a distribution; and estimating a property of a formation from the distribution, wherein the formation comprises a distribution of pore sizes of about 10 nm or more, and wherein the property comprises natural gas composition.

Some embodiments may have relaxation times that are about 0.1 msec to about 10,000 msec and/or the relaxation times are of the same order of magnitude of the inter-echo time. In some embodiments, the formation comprises a core, cuttings, material in communication with a wellbore, or a combination thereof. In some embodiments, the formation comprises shale, coal, kerogen, or a combination thereof. In some embodiments, the formation comprises a distribution of pore sizes of about 10 nm or more.

Some embodiments may form an hydrogen index which may include observing controlled temperature and pressure samples. The samples may include core, cuttings, or a combination thereof.

In some embodiments, the methods may include analyzing a mud log, performing a fluid analysis in a wellbore, using fluid collected from a wellbore, performing resistivity measurements and/or performing dielectric measurements.

FIGURES

Figure 4A:
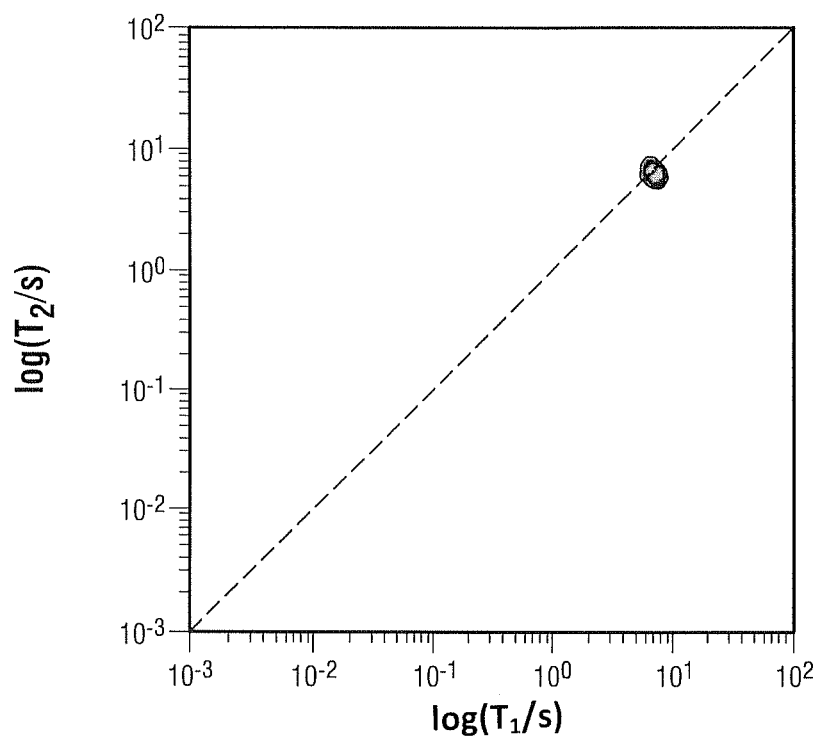
Figure 4B:
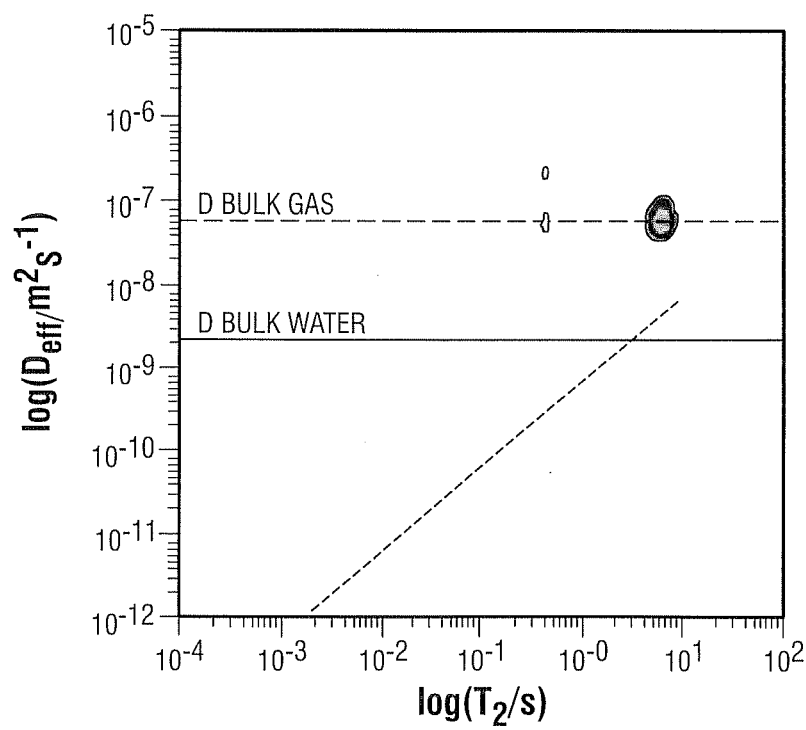
Figure 5A:
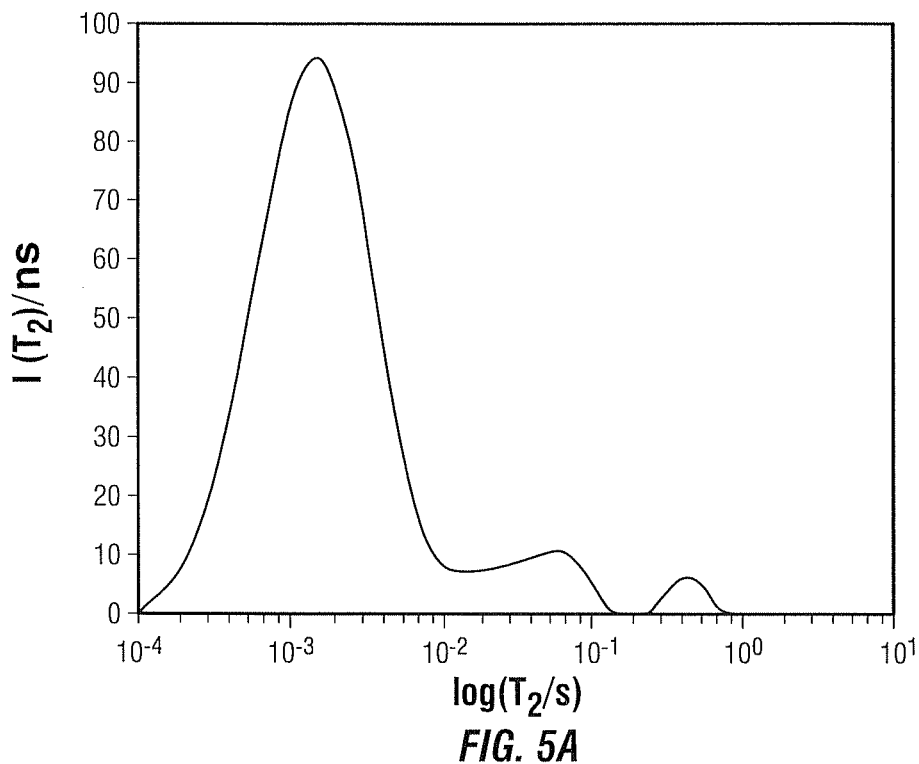
Figure 5B:
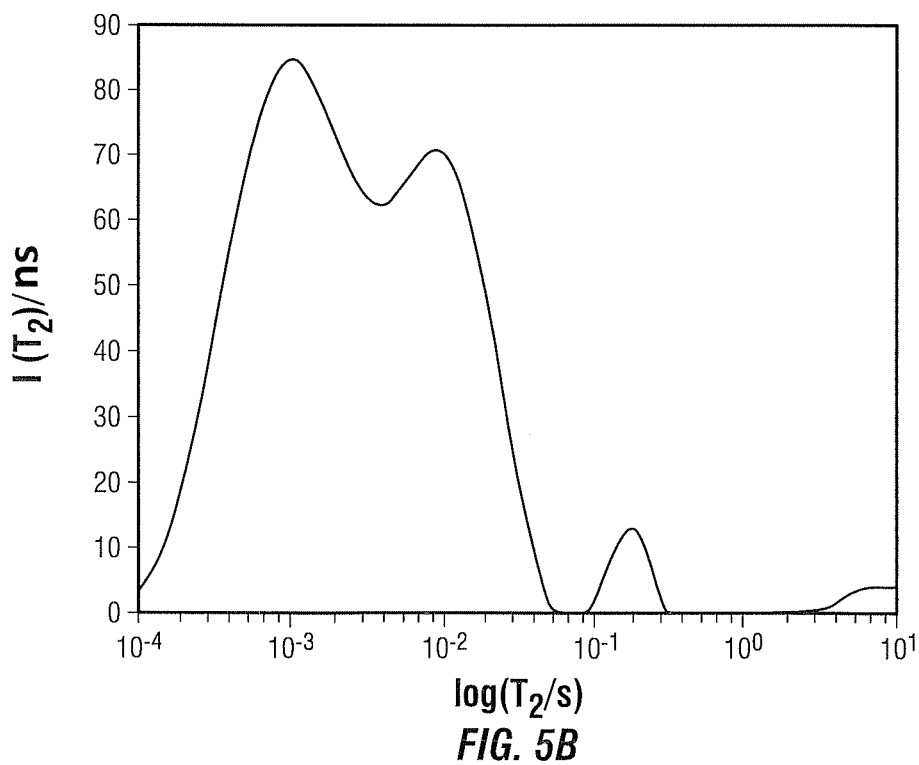
Figure 5C:
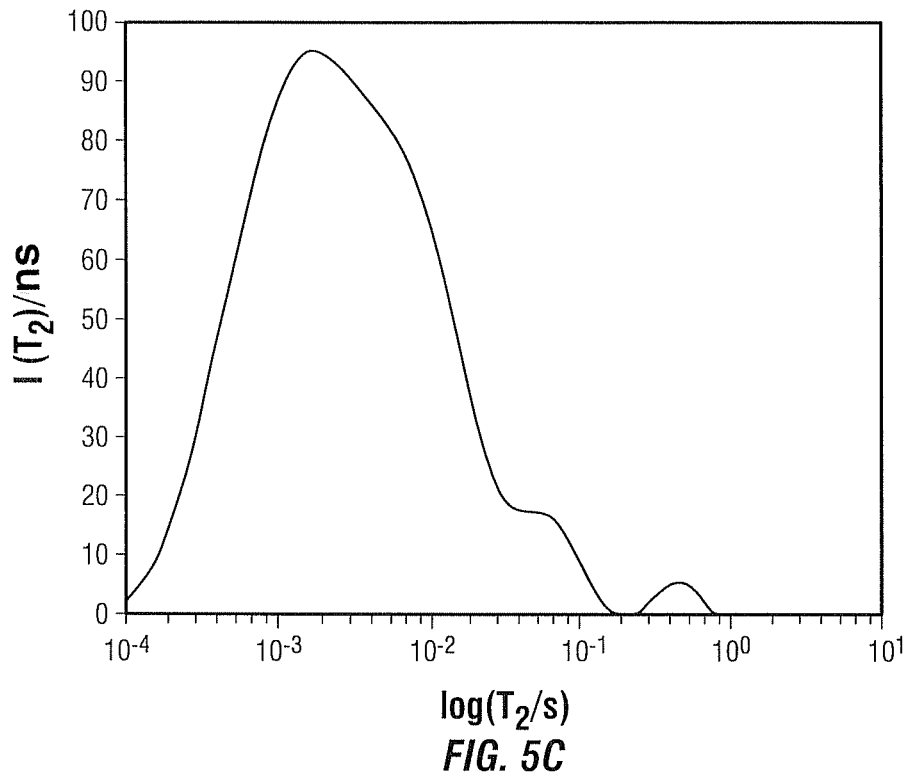
Figure 5D:
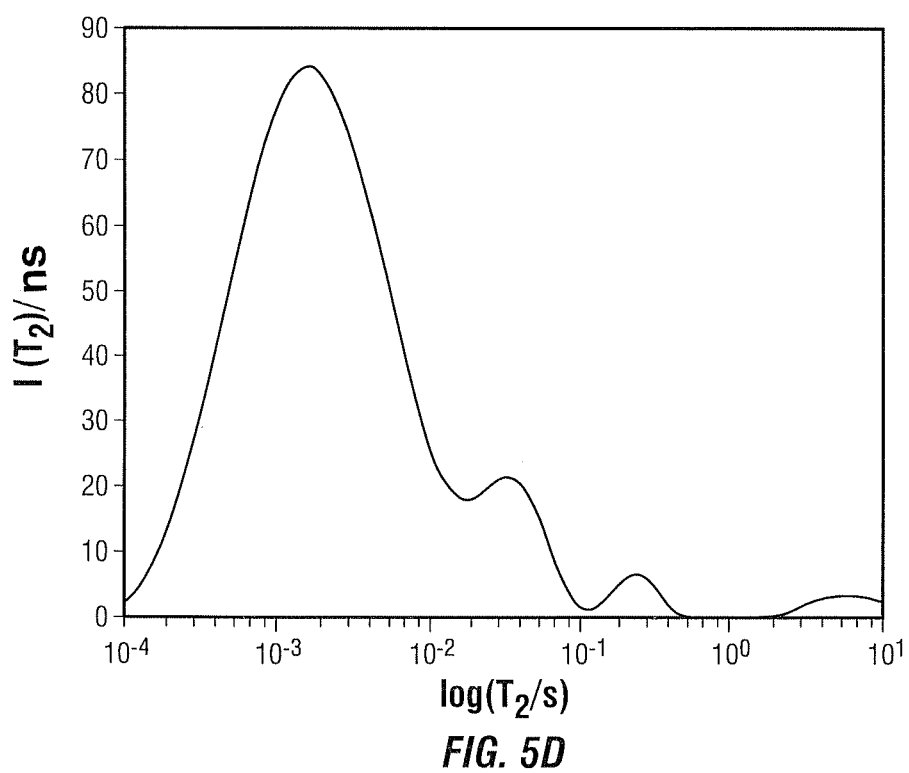
Figure 6A:
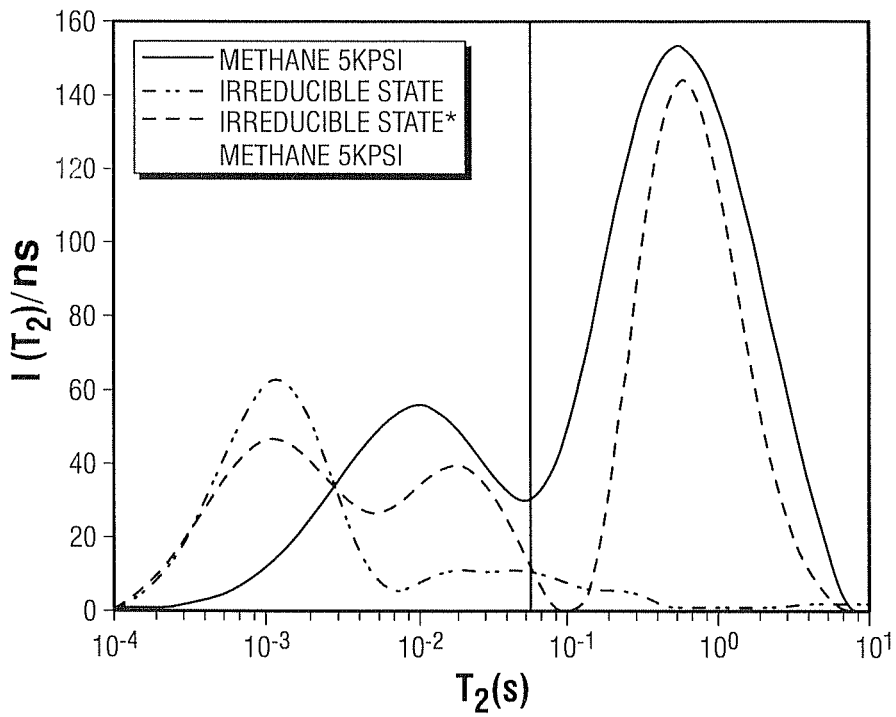
Figure 6B:
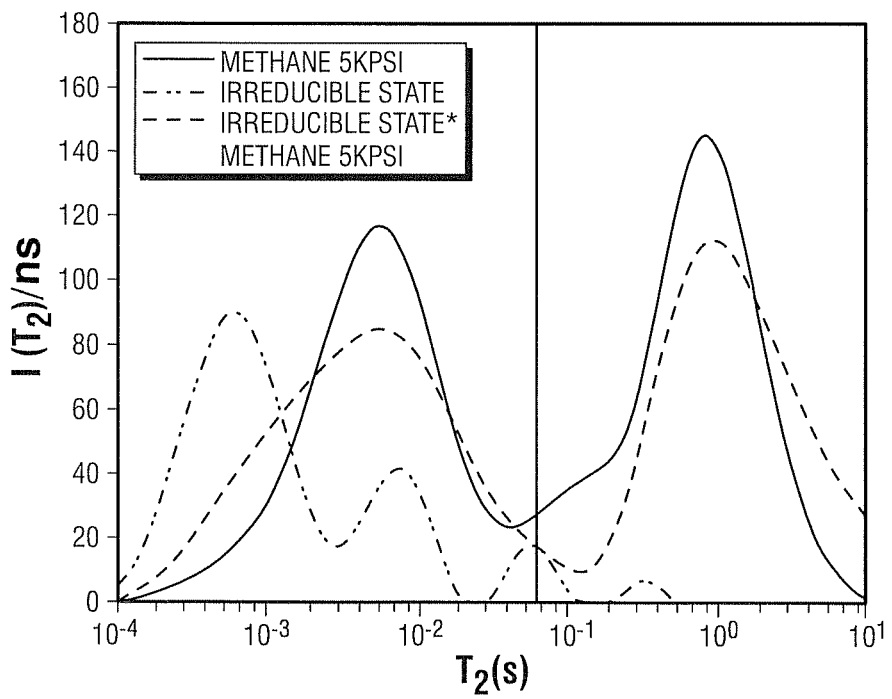
Figure 6C:
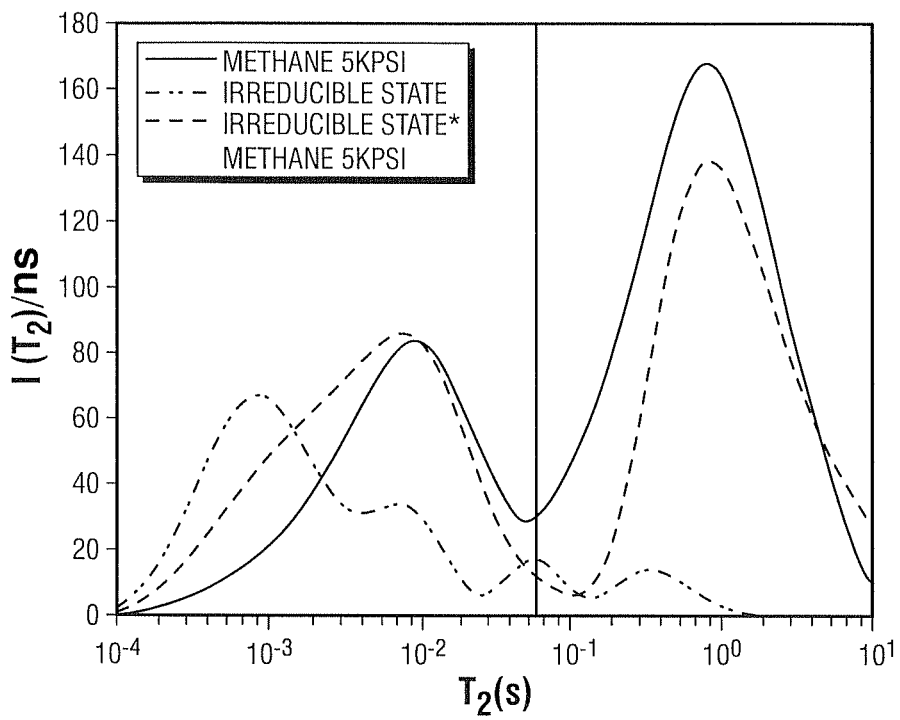
Figure 6D:
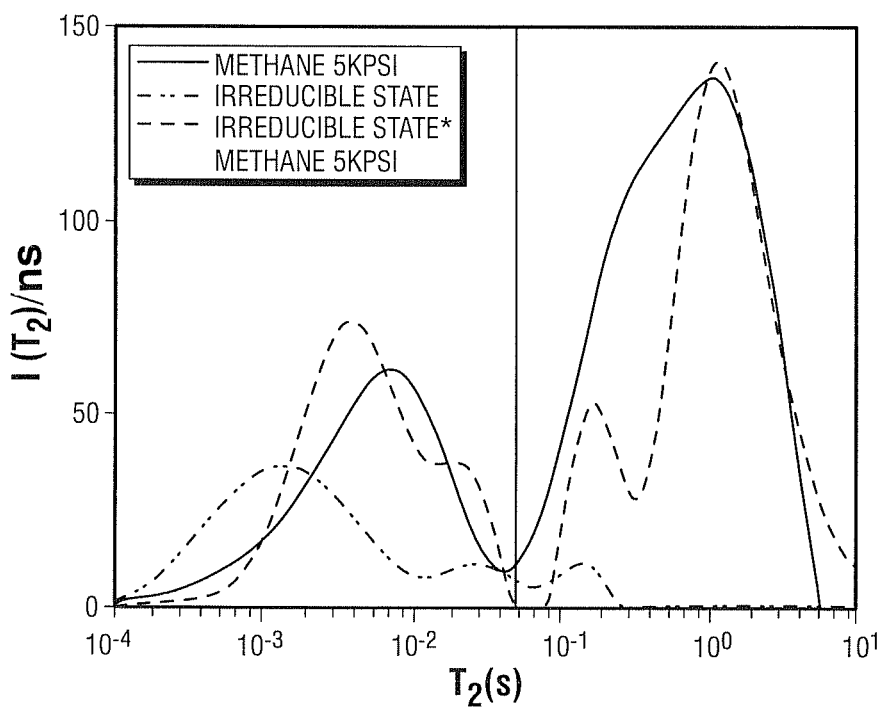
Figure 7A:
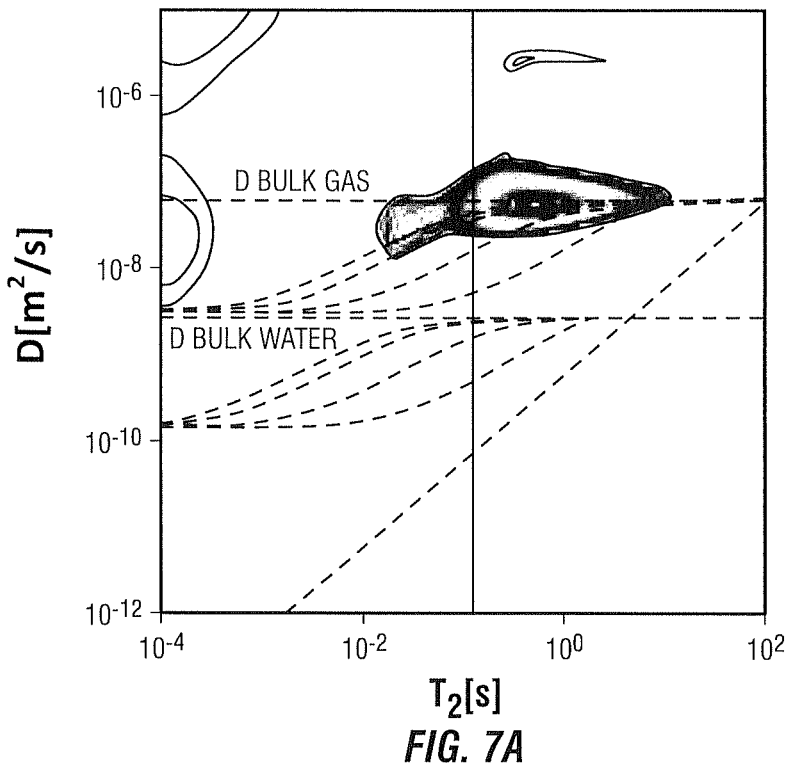
Figure 7B:
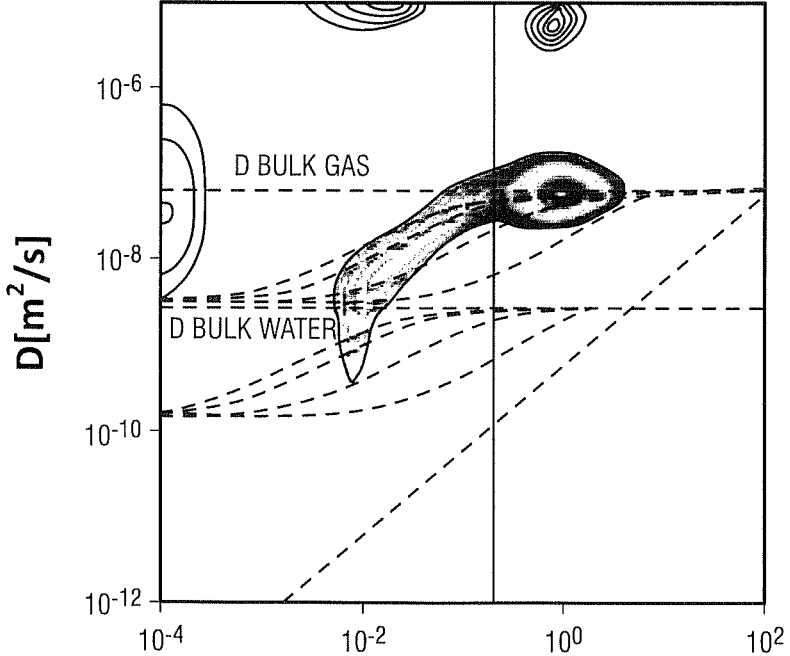
Figure 7C:
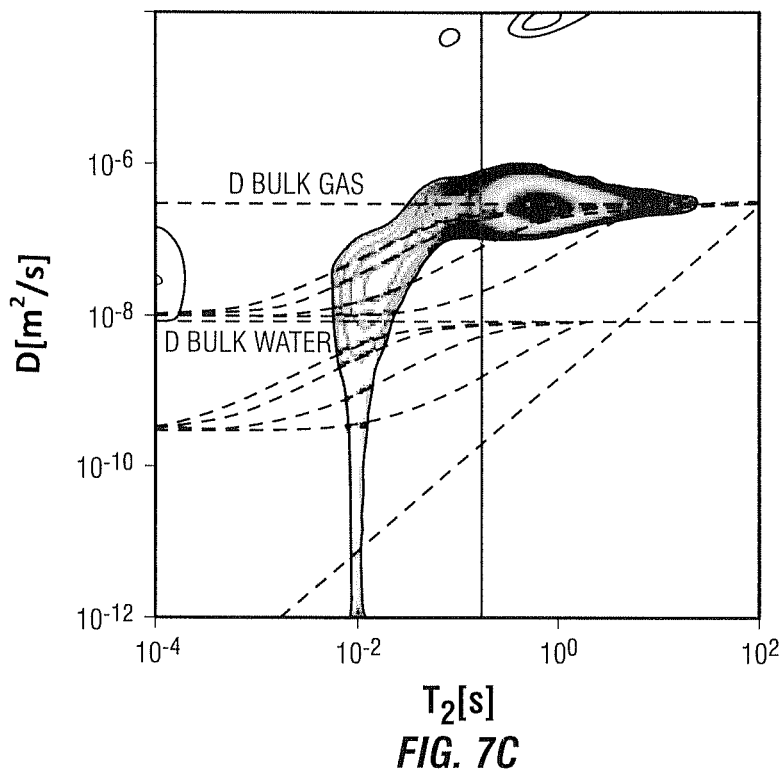
Figure 7D:
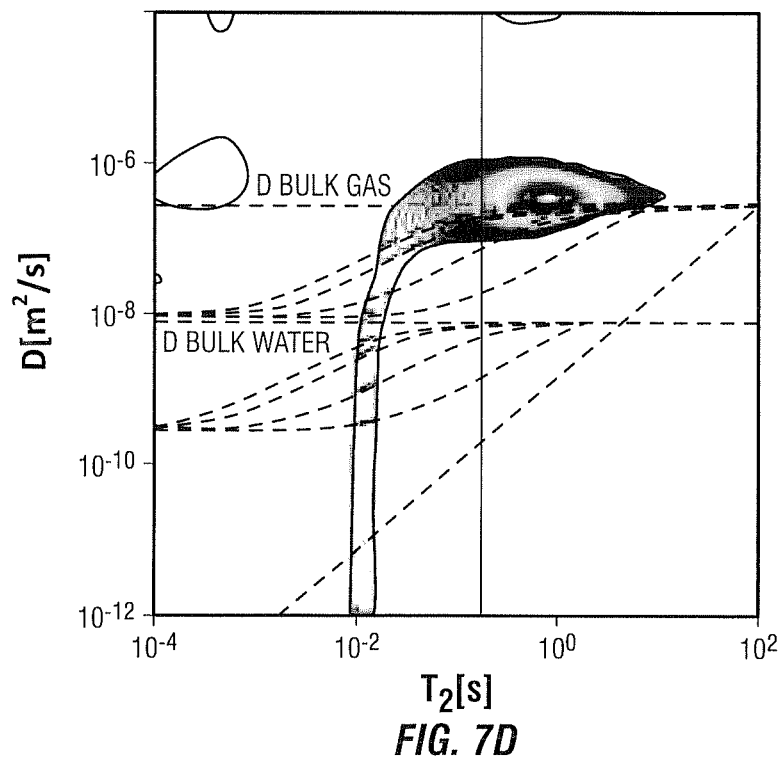

FIGS. 4A and 4B are respective a bulk methane gas T1-T2 plot and D-T2 plot. FIG. 4A clearly shows the signal falling on the diagonal line as T1=T2 for the bulk, motionally averaged gas. FIG. 4B shows the bulk gas diffusion coefficients at 5 kpsi and 30° C. to be clearly an order of magnitude larger than the values for bulk water.

FIGS. 5A-5D are brine-saturated T2 distributions for all four gas shale plugs studied. The distributions are peaked around 1 ms indicating the strong surface relaxation of the fluid in the nanoscale pores.

FIGS. 6A-6D are plots showing brine (irreducible state) and methane-saturated T2 distributions for all the four gas shale plugs. Brine (irreducible state) and methane saturated states have T2 distributions peaked about 1 ms and 10 ms and with overlap between the distributions. The methane saturated samples with brine (irreducible state), also clearly shows that the signals are not well separated in the T2 dimension.

FIGS. 7A-7D are D-T2 plots for the methane gas inside the gas shale samples. The restricted diffusion formalism has been applied for both the gas and water for the four different surface relaxivity values of 1 um/sec, 10 um/sec, 50 um/sec and 100 um/sec. The data to the left of the vertical line is the relevant contribution from the fluids in the gas shale.

Figure 8A:
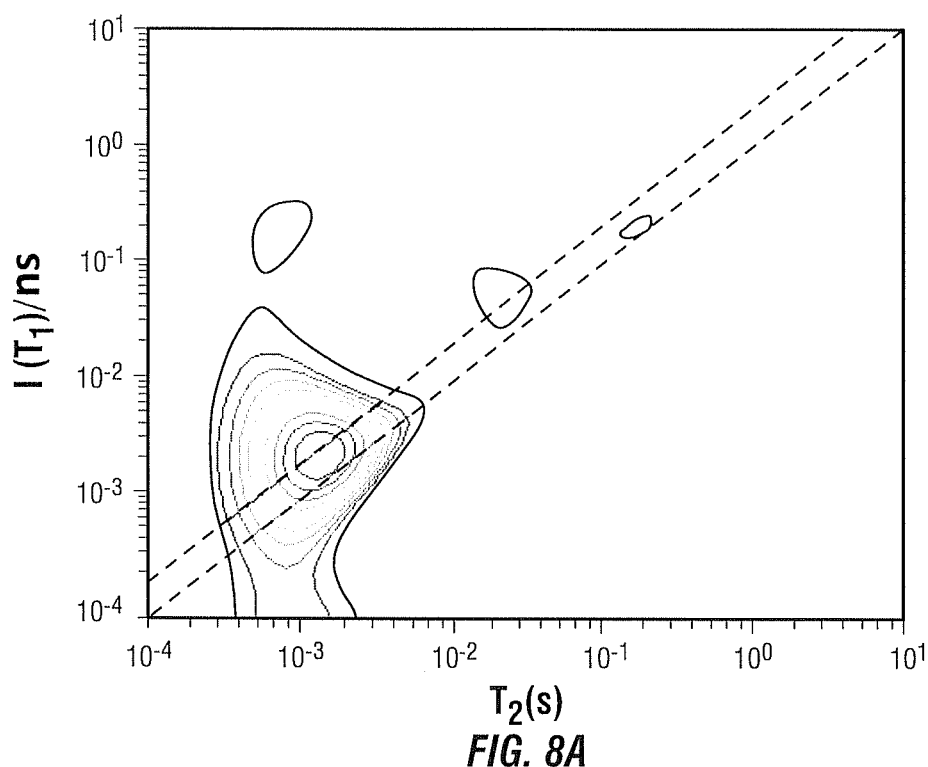
Figure 8B:
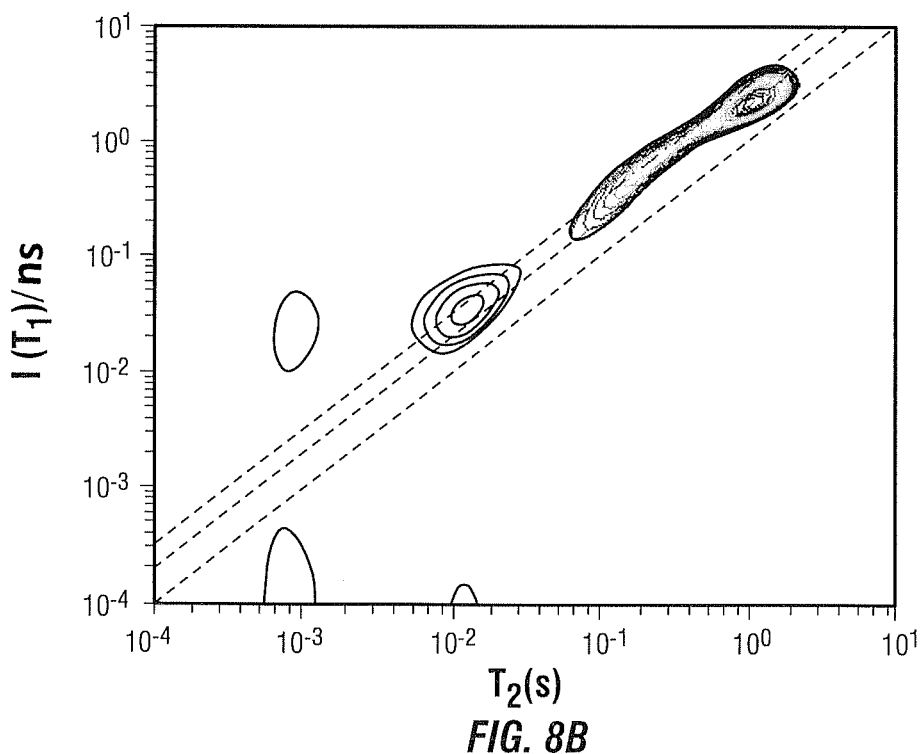

FIGS. 8A and 8B are T1-T2 maps of the brine (irreducible state) and methane-saturated state for one of the gas shale plugs. The T1-T2 experiments enable the application of cutoffs in both the relaxation dimensions for the separation of the fluids.

Figures 9A, 9B, 9C, 9D:
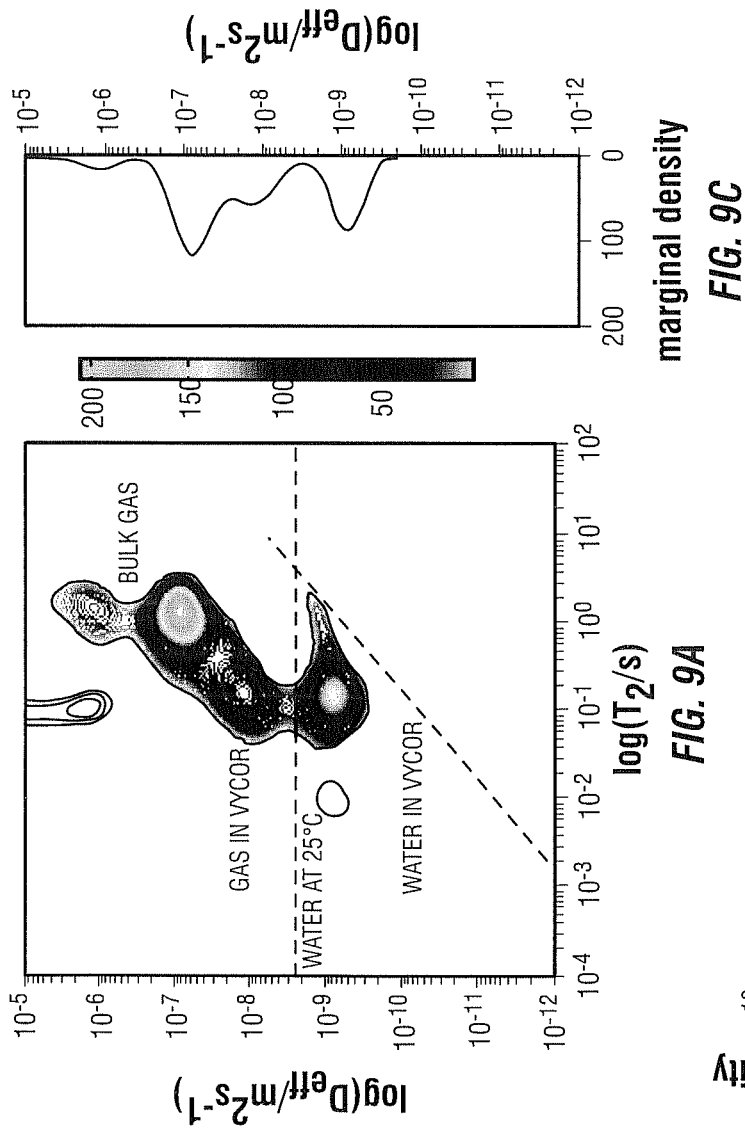

FIG. 9A is a D-T2 map of brine and gas saturated in 4 nm Vycor glass beads, while FIGS. 9B and 9C are respectively plots taken from data of FIG. 9A of T2(s) and a function of diffusion D versus marginal density, and FIG. 9D is a SEM picture of Vycor porous glass. FIG. 9C shows that the brine and gas contributions are well separated in the diffusion dimension even though, as seen in FIG. 9B, they overlap in the relaxation dimension, exhibiting the potential of 2-D NMR D-T2 experiments for such applications.

Figures 10A, 10B:
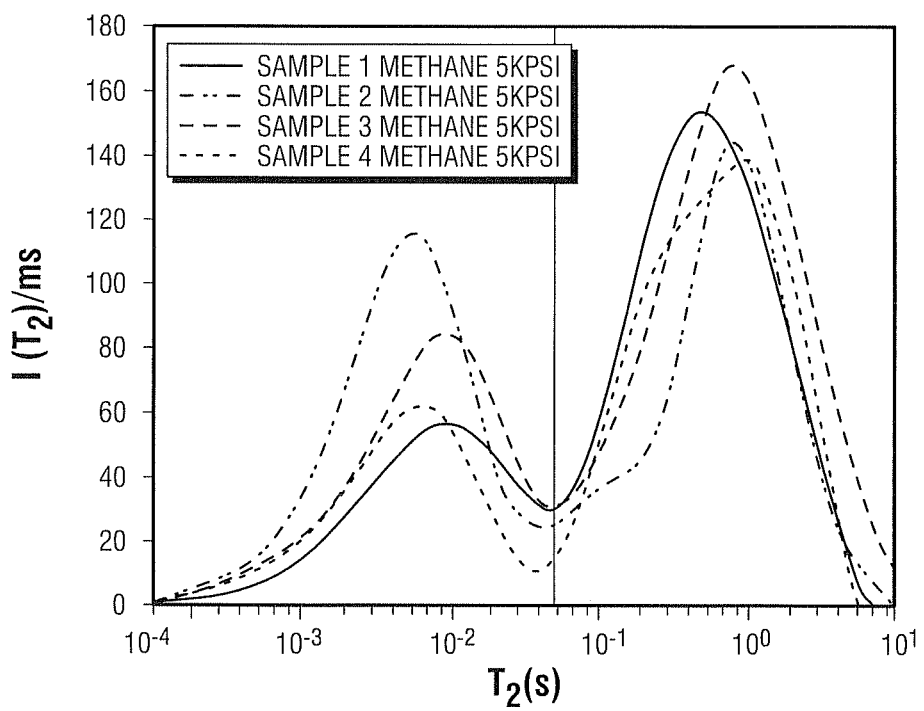

FIGS. 10A and 10B are respectively a chart and plot showing the correlations between the T2 distributions in the different gas shales with their clay, carbonate and total organic content and their surface to volume ratios.

DESCRIPTION

At the outset, it should be noted that in the development of any such actual embodiment, numerous implementation—specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary of the invention and this detailed description, each numerical value should be read once as modified by the term "about" (unless already expressly so modified), and then read again as not so modified unless otherwise indicated in context. Also, in the summary of the invention and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

The statements made herein merely provide information related to the present disclosure and may not constitute prior art, and may describe some embodiments illustrating the invention.

We provide understanding of the measurement effects of gas shale through lab experiments and devise techniques to quantitatively log these unconventional plays in this application. We also determine the average hydrogen index of the gas in the gas shale pores under certain lab conditions and discuss how they can be used in downhole logs with NMR and other techniques for evaluating the hydrocarbon response. Thus in this invention we propose optimal ways of logging gas shales with T2, T1, T1-T2, DT1 and DT2 logs, interpretation techniques based on the hydrogen index and propose how they can be complemented with other logs like resistivity, dielectric, density and neutron etc for downhole fluid determination.

We studied the NMR responses of water and methane in core plugs taken from a gas-shale formations and established methodologies for dealing with the formations. NMR T2, T1 and diffusion data were acquired at pressures up to 5 kpsi on core plugs in their methane saturated, water saturated, centrifuged, then re-saturated with methane states, to study separately the effects of bound water and gas in nanopores. Hydrogen index of the gas is estimated from a few different methods including comparison of 100% water-saturated and 100% methane-saturated NMR porosities and comparison of gas filled NMR response with porosities obtained from conventional methods. The goals were to find better ways of obtaining NMR information downhole and their petrophysical applications and to also determine and use the hydrogen index for lab and downhole petrophysics.

A methodology is used for optimal logging methods and interpretation in unconventional plays like gas shale for the gas, water and oil response. Application of NMR logging like $T_1$, $T_2$, $T_1$-$T_2$, $DT_2$, $DT_1$ with optimized parameters are proposed for better logging of these reservoirs. A methodology for the acquisition of an average value for the hydrogen index of the gas in the gas shale under certain conditions has been proposed and its application in various downhole logs is discussed. Application of other techniques like dielectric, resistivity, density and neutron are used to complement NMR for the determination of fluid volumes downhole is also discussed.

Some embodiments may benefit from NMR tools including CMR, MRX, Magnetic Resonance Scanner, and/or Pro-Vision commercially available from Schlumberger Technology Corporation of Sugar Land, Tex. Some embodiments may benefit from additional tools including AIT, RT Scanner, and/or the dielectric scanner commercially available from the Schlumberger Technology Corporation of Sugar Land, Tex.

NMR Relaxation Properties of Gas Molecules in Gas Shale

The dominant mechanism of NMR relaxation in bulk methane is spin rotation. The basis of this mechanism is that when a molecule rotates, the motion of the electron cloud in the molecule generates a magnetic field at the position of the nuclei. The molecular rotations produce a time-dependent field at the nucleus, which is a small perturbation to the applied field, causing the relaxation of the nucleus. In cases where the pressure of the bulk gas is increased, increased collisions between gas molecules occur and molecular rotations are disturbed. This reduces efficiency of the spin rotation mechanism and results in longer relaxation times.

Figure 1A:
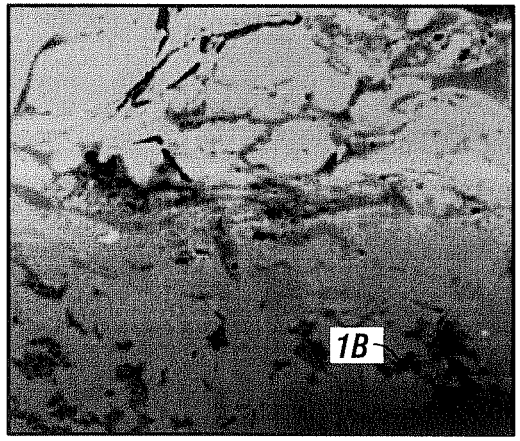
FIGS. 1A and 1B are respectively a SEM picture depicting kerogen patches in a matrix which host the dominant porosity and a conceptualized picture of the free and adsorbed gas in a kerogen pore.
Figure 1B:
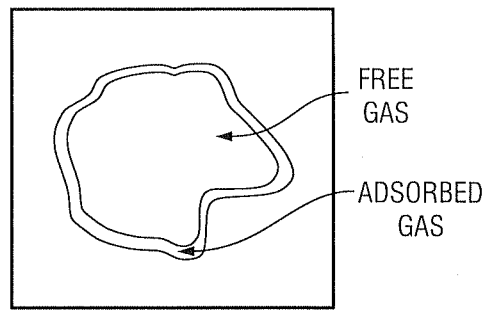

When the gas is confined in the nanopores of gas shales, the dominant mechanism of relaxation is no longer spin rotation but surface relaxation. The strong dipolar interaction of the gas molecules with paramagnetic impurities and protons of the kerogen, enhanced by the high surface-to-volume ratios, strongly influences the relaxation mechanism. As surface relaxation is a much stronger relaxation mechanism than spin rotation, this results in large reductions of the relaxation times from their bulk values. Another important phenomenon to be considered for gas at high pressure is that of adsorption on the pore surface. The behavior of methane adsorption on the surface of gas shale pores can be approximated by Langmuir isotherm behavior. This mechanism results in about a monolayer of methane being formed on the surface of the pores. Adsorbed gas has much shorter relaxation times than free gas due to the strong interaction with the pore surface. As FIGS. 1A and 1B illustrate, the surface of the pore may have a higher density or concentration of gas as the gas interacts with the pore surface. Because the pore surface may be wet with hydrocarbon and/or have a higher pore surface area to pore volume than other formation types, some formation types that may benefit from processes described herein include shale, shale gas, coal, kerogen, or any hydrocarbon wet formation.

Figure 2:
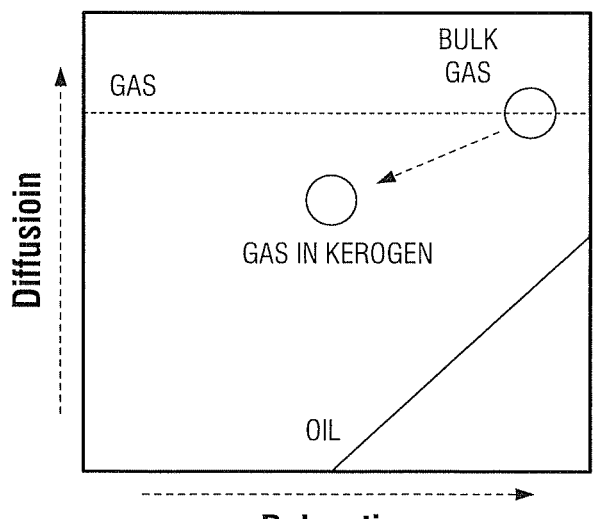
FIG. 2 is a schematic 2D-NMR plot for gas inside gas shales showing reduced diffusion coefficients and relaxation times as a result of adsorption, surface relaxation and restricted diffusion in the small pore sizes.

The gas molecules in the kerogen nanopores are adsorbed or free at any given instant of time as shown in FIG. 2. However, the two populations are in fast exchange with each other. Thus, the resulting relaxation can be expressed as Thus, the resulting relaxation can be expressed as $$\frac{1}{T_{i,eff}} = \frac{1-\varepsilon}{T_{i,free}} + \frac{\varepsilon}{T_{i,adsorbed}}, \quad (1)$$

where $\varepsilon$ is the fraction of molecules in the adsorbed phase and $1-\varepsilon$ the fraction of non-adsorbed molecules in the pore interior and i is 1 or 2 depending on whether $T_1$ or $T_2$ is being considered. The net relaxation times inside the pores are dominated by surface relaxations and can also be expressed as $$\frac{1}{T_i} = \frac{1}{T_{i,bulk}} + \frac{\rho_i S}{V}, \quad (2)$$

where i is 1 or 2 depending on whether $T_1$ or $T_2$ is being considered, and $\rho_i$ the surface relaxivity and S/V the surfaceto-volume ratio. In this case we have ignored the effect of any applied or internal gradients. The effect of applied and internal gradients, if present, would not have any impact on the longitudinal spin-lattice relaxation time $T_1$ but will affect $T_2$. Thus the relation for $T_2$ in the presence of gradients, either internal or externally applied, is given by $$\frac{1}{T_{2,pore}} = \frac{1}{T_{2,bulk}} + \frac{\rho_2 S}{V} + \frac{(\gamma G T_E)^2 D}{12}, \quad (3)$$

where the last term takes the effect of diffusion dephasing on $T_2$ into account.

NMR Diffusion Properties of Gas Molecules in Gas Shale.

The diffusion dynamics for gas in gas shale is different from the bulk gas behavior. This is because the gas in gas shale exists in two phases, absorbed on the pore surface and the other as free gas in the pore interiors. The net diffusion coefficients are a sum of the contributions in both these phases and are modulated by their exchange. The free gas in the pores can exhibit the short or long time limit diffusion behavior depending upon the NMR diffusion encoding times used. The free gas diffusion can also be dominated by Knudsen or bulk diffusion characteristics depending upon whether the mean free path is larger or smaller than the pore diameters. The diffusion dynamics of the adsorbed gas might be mainly through the mechanism of thermal hopping on the surface.

The diffusion coefficient of bulk gas is about $6 \times 10^{-8}$ m$^2$/s at 30° C. and 5 kpsi, which is an order of magnitude greater than that of bulk water. The high diffusion coefficients of bulk gas can be exploited to separate gas from other fluids with lower diffusivity such as oil and water in 2D-NMR experiments. For the free gas phase, the mean squared displacement of the diffusing molecules acquire time dependence and the quantity defined by the Einstein relation is referred to as the time-dependent diffusion coefficient. For short times, i.e., when the diffusion length scale is much smaller than the pore size scale, the diffusion coefficient is reduced from its bulk value D0 by an amount proportional to the total surface-to-volume ratio S/V of the pore space $$D(t) = D_0 \left[ 1 - \frac{4}{9\sqrt{\pi}} \frac{\sqrt{D_0 t} S}{V} \right]. \quad (4)$$

However, this regime is generally not encountered for gas diffusion in the kerogen pores of gas shales because the pore scales are very small in comparison to the root-mean-square displacements during diffusion encoding time. In the case of a connected pore system, the long time limit diffusion coefficient approaches the tortuosity limit given by $$D(t \to \infty) \approx \frac{D_0}{\tau}, \quad (5)$$

where $\tau$ is called the tortuosity of the medium and is related to the formation factor F and the porosity $\phi$ by $$\tau = F\phi \quad (6)$$

In gas shale, the diffusion is in the tortuosity limit as the heterogeneity length scales are short compared to the root mean square displacements during NMR encoding time. We next consider the limiting cases of Fickian (bulk) and Knudsen diffusion regimes. The case of Fickian diffusion occurs when the molecule-molecule collisions are dominant due to the mean free path being smaller than the pore dimensions ($\lambda \ll d$). On the other hand, Knudsen diffusion, occurs when the molecule-surface collisions are dominant due to the mean free path being larger than the pore dimension ($\lambda \gg d$). In the tortuosity limit the two regimes are given by $$D_k = \frac{D_{0k}}{\tau_k}, \text{ and } D_b = \frac{D_{0b}}{\tau_b}, \quad (7)$$

where the subscript k denotes "Knudsen" and the subscript b denotes "Fickian or bulk". Depending on the pore sizes in gas shales and the mean free path of the gas molecules, we could be in one of the above two regimes or in the transition regime between the two. Pore filling resulting from adsorption on the pore surfaces would decrease the effective diameter d and the Knudsen diffusion coefficient.

The adsorbed gas phase on the pore walls can also have its own diffusion dynamics. The surface diffusion mechanism is known to play an important role in mass transport through porous media and is associated with thermally activated hopping. The net diffusion coefficient is a function of the exchange time and bulk and surface diffusion mechanisms. The net diffusion coefficient can be written as the sum of the diffusion in each phase weighted appropriate $$D_{eff} = (1 - \in) D_{gas} + \in D_{ad}, \quad (8)$$

where $1 - \in$ and $\in$ are the respective fractions in the gas and adsorbed phases respectively, and $D_{gas}$ and $D_{ad}$ are the corresponding diffusion coefficients.

Experimental Setup and Methodology

The NMR laboratory experiments were done on a 2.2 MHz Oxford Instrument's Maran-2 spectrometer. The spectrometer was also equipped with gradient coils enabling application of strong magnetic field gradients of up to 50 Gauss/cm axially along the bore. The pressure cell for holding the sample is designed such that that it can fit inside the magnet bore. The maximum pressure applied in our experiments was 5 kpsi. At the beginning of the experiment, a vacuum pump is attached to de-gas the entire setup. Oxygen, which is paramagnetic and thus could act as a strong relaxation agent even in small quantities, resulting in measurable reduction of the relaxation times of the methane gas, needs to be completely removed. Thus, care is taken to make sure that there is no oxygen present in the system when methane gas is measured. Once evacuated, 99.99% ultra pure methane is let into the system. This cycle of evacuation and injection of methane is repeated four times so that no trace of oxygen remains in the system. At the end of this process, the setup is filled with methane gas again and a hydraulic pump is used to compress the gas in the accumulator and the NMR cell. This results in high pressure gas in the NMR cell which can then be inserted into the magnet bore of the Maran spectrometer. The spectrometer also has temperature control capability with a range from 30° C. to 120° C. Heating is achieved by passing dry air through a heater from under the magnet and then passing the heated air onto the sample. A thermocouple is present close to the magnet bore to monitor the temperature of the sample.

The experiments on gas shale were performed on four core gas shale samples. The samples of a foot in length were cut out from four different depths and Hassler size plugs (1.69 in.×0.69 in.) were drilled out of these cores. The samples were then preserved in sealed containers until they were used in the experiments. The gas shale plugs were inserted in a tight fitting PEEK container and placed in the NMR cell. Though the sample fits snugly in the PEEK container there was a small amount of gas trapped in the annulus between the sample and the holder, which is referred to as the dead volume henceforth.

Spin-spin relaxation times or $T_2$ are measured using a Carr-Purcell-Meibolm-gill (CPMG) sequence. Both 2D-NMR experiments such as $T_1$-$T_2$ and D-$T_2$ were also carried out on bulk gas and water/gas confined in the plugs. The pulse sequence used for $T_1$-$T_2$ experiments consists of an inversion recovery period to encode for $T_1$ followed by the CPMG echo train to measure $T_2$. For the D-$T_2$ experiments, pulse field gradients (PFG) were used for diffusion encoding. This is because the MARAN spectrometer has a homogenous magnetic field as opposed to the steady gradients found in downhole NMR tools. PFG-NMR technique involves the application of pulsed gradients (as opposed to the steady gradients) to non-invasively measure the ensemble average molecular mean square displacement of the spin bearing molecules of interest and has been extensively used to study diffusion of molecules in porous media. The applied gradients and the encoding times can be effectively adjusted to replicate the results that would be obtained using steady gradient diffusion logging on NMR downhole tools. The pulse gradients were varied from 0-50 G/cm in the axial direction. The sequence used here consists of two RF pulses, first the 90 and then the 180 each followed by a gradient pulse of 2.5 ms duration to encode diffusion. This sequence is then followed by the CPMG echo train of 5000 echoes to measure $T_2$. The $T_1$-$T_2$ experiments were carried out by applying an inversion recovery pulse sequence followed by the CPMG train. All data were processed using Inverse Laplace Transform to obtain 1D and 2D plots. Some embodiments may benefit from a pulse sequence selected for fast relation times such as the methods described in "Improved Precision Magnetic Resonance Acquisition: Application to Shale Evaluation" by Peter Hook, David Fairhurst, Erik Rylander, Rob Badry, Nate Bachman, Steve Crary, Kirck Chatawanich, and Tim Taylor, presented at the SPE Annual Technical Conference and Exhibition held in Denver, Colo. on Oct. 30-Nov. 2, 2011 by the Society of Petroleum Engineers available with the journal number SPE 146883, which is incorporated by reference herein.

Experimental Results

1. NMR Measurements of Bulk Gas

We used pure methane gas for the experiments, which is a reasonable approximation for natural gas, since methane is a major component of natural gas. In our experiments, which are conducted at pressures from 1 kpsi to 5 kpsi and at a temperature of 30° C., methane exists as a supercritical fluid. The bulk methane gas at the pressure and the temperature conditions specified, is therefore not an ideal gas.

Its physical properties, including the variation of relaxation times with pressure and temperature, have already been well characterized experimentally (Gerritsma et al., 1971).

Figure 3A:
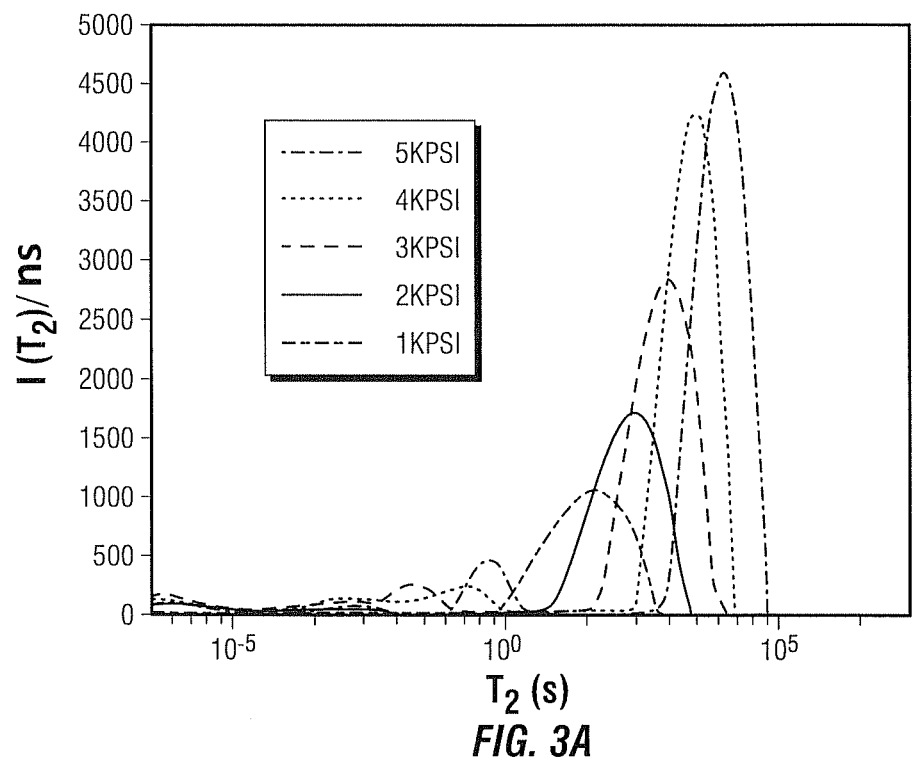
FIGS. 3A and 3B are respectively plots of the T2 distributions of bulk methane and T2 peak amplitudes versus pressure Both the T2 peak amplitude and intensity of the T2 distributions increase with pressure.
Figure 3B:
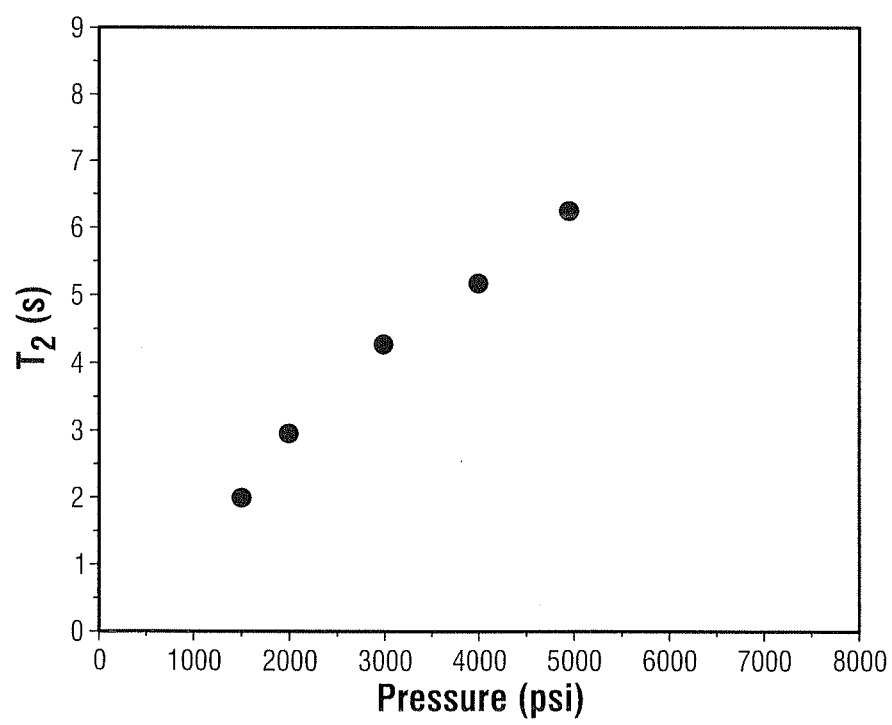

The measured $T_2$ distributions are shown in FIG. 3A. In FIG. 3B, the absolute values of $T_2$ corresponding to the maximum of the distributions are plotted as a function of pressure. The bulk methane gas $T_1$ values are equal to that of $T_2$ due to motional averaging and the peak is on the diagonal line as expected, in the $T_1$-$T_2$ plot shown in FIG. 4A. The D-$T_2$ map is shown in FIG. 4B. The diffusion coefficient of bulk methane gas at 5 kpsi and 30° C. is $6\times10^{-8}$ m$^2$/s, which is more than an order of magnitude greater than that of bulk water at the same temperature.

2. NMR $T_2$ Measurements of Gas Filled Shale Plugs

We next investigated the relaxation dynamics of methane inside the gas shale samples. Hassler size plugs (1.69 in.×0.69 in.) were drilled out of these cores for the measurements. The samples were then heated to 60° C. under vacuum overnight to remove any trace moisture in them. Methane gas at 5 kpsi was injected into the samples and the $T_2$ relaxation times of the completely gas saturated samples were measured. The results of the methane relaxation times for all the four plugs are shown in FIGS. 5A-5D. Because of the very low permeability, $T_2$ measurements were carried out periodically until there was no change in the $T_2$ spectrum, indicating attaining equilibrium state. The samples were then evacuated and taken out for pressure saturation with brine. Saturation of the plugs with brine at 250 ppk to avoid clay swelling was carried out over a 24 h period at 1.2 kpsi. $T_2$ distributions of the brine saturated samples are shown in FIGS. 5A-5D.

The samples were centrifuged at 340 psi (irreducible state) and the $T_2$ distributions measured are shown in FIGS. 6A-6D (dash-dot-dash curves). Next, methane gas was injected into the plugs (which are at irreducible state), and the gas pressure maintained at a value of 5 kpsi. The T2 experiments were done at 30° C. with long wait times of 30 s, inter-echo times of 0.4 ms and 15000 echoes. The results are shown in FIGS. 6A-6D (dashed curves). The relevant part of the distribution is from 0.1 ms to 100 ms and is the important fraction for job planning and anything larger than 100 ms is from the larger length scales and the annulus dead volume between the sample and the peek sample holder. The gas T2 distribution is peaked around 10 ms and the bound water is peaked about 1 ms.

3. D-$T_2$ of Gas in Gas Shale Plugs

2D NMR D-$T_2$ results of the gas shale samples are shown in FIGS. 7A-7D. The reduction in diffusion coefficients is caused by restricted diffusion and surface adsorption. The restricted diffusion lines for gas (upper dashed lines between $10^{-9}$ and $10^{-7}$) and water (lower dashed lines starting at $10^{-10}$) without taking adsorption into account has been plotted for different surface relaxivities. The experiments were carried out with wait times of one second, which is sufficient to completely polarize the methane inside the gas shale plugs (the species of interest) but not the free gas in the dead volume.

4. $T_1$-$T_2$ of Gas in Gas Shale Plugs

2D-NMR $T_1$-$T_2$ experiments of the gas in gas shale and of the BFV for Sample#1 is shown in FIGS. 8A and 8B. The 2D NMR experiments enable the application of cutoffs in both the relaxation dimensions ($T_1$ and $T_2$) and thus lead to better separation of the fluids.

5. NMR Measurements on Vycor

To understand the effects of adsorption and surface relaxation in the organic kerogen pores, experiments were also carried out on methane gas confined in Vycor porous glass, for the purpose of comparison. The Vycor porous glass (see FIG. 9D) is made up of pure silicon oxide and has a known pore size of 4 nm which is comparable to the smallest pore sizes encountered in gas shales. The pulse sequence parameters such as wait times and inter-echo times were kept the same as in the case of the gas shale samples. It is interesting to note that relaxation time of the gas molecules restricted inside the pores of the Vycor glass sample are peaked at around 100 ms, which is 10 times longer than in the case of methane in the gas shale samples (see FIGS. 9A and 9B). The relaxation distribution for the fluids in the Vycor porous glass is narrow, reflecting the homogeneous 4 nm pore size of the sample. Note that the gas and water T2 distributions overlap (FIG. 9B) and thus cannot be separated in the relaxation dimension. Though both water and gas have lower diffusion coefficients compared to their respective bulk values due to restricted diffusion, they are well separable in the diffusion dimension (FIG. 9C).

Hydrogen Index Measurement

The nuclear magnetic resonance (NMR) lab and logging tools measure signal amplitude which is proportional to the density of hydrogen nuclei of the sample. In order to obtain sample quantities (e.g. volumes and eventually porosities) the hydrogen index has to be known. Different fluids have different Hydrogen indices and they also vary as a function of temperature and pressure. The Hydrogen index of formation water and different crude oils have been tabulated for different conditions. Natural gas in bulk like state tends to have a significantly lower hydrogen index whose dependence on pressure and temperature is known in prior art. But for natural gas in unconventional plays like gas shales and coal bed methane or other tight gas plays it is challenging to obtain the hydrogen index at specific pressures and temperatures existing downhole.

If the quantity of fluids in the rock is known then the porosity (fluid volume/rock volume) can be determined. Traditionally the NMR tools have been calibrated to 100% porosity with water at the surface, whose hydrogen index is assigned a value of one. NMR porosity logs can therefore be obtained downhole, by comparing the measured $T_2$ response for each fluid with the calibrated 100% porosity.

Here we consider only the case where the reservoir fluids are the irreducible water and gas. In the case of some oil (base or invaded) being present the same analysis can be extended. The NMR determined porosity in this case is given by)

$$\phi_{MR}=HI_wV_w(1-e^{-p/T1w})+HI_gV_g(1-e^{-p/T1g}) \quad (9)$$

where $HI_w$ and $HI_g$ are the hydrogen index of the water and gas phase, $V_w$ and $V_g$ are the respective volumes, p is the wait time, $T_1$ is the spin lattice relaxation time and $1-e^{-P/T1}$ takes care of the insufficient polarization times. Eqn (9) can be rewritten as $$\phi_{MR}=HI_w(1-S_g)\phi(1-e^{-p/T1w})+HI_gS_g\phi(1-e^{-p/T1g}), \quad (10)$$

where $S_g$ is the gas saturation and $\phi$ is the actual porosity, i.e. the volumetric fraction of the rock that is pore space. In the case of complete polarization of the spins the NMR measured porosity is given by $$\phi_{MR}=HI_w(1-S_g)\phi+HI_gS_g\phi. \quad (11)$$

The above equation can also be written as $\phi_{MR}=\phi_{MR(water)}+\phi_{MR(gas)}$. In the above equation both the water saturation ($S_w=1-S_g$) and the hydrogen index are unknown. If the gas and water contributions can be separated in the T2 or T1 dimension then the water saturation can be determined. But it has been shown that there can be significant overlap making this separation difficult in many cases. To overcome this problem and determine the water saturation many different logging techniques can be used in combination, as will be discussed below. If the water saturation can thus eventually be determined then the apparent NMR gas filled porosity can be expressed a $$\phi_{MR(gas)}=HI_gS_g\phi. \quad (12)$$

Therefore, knowledge of the gas phase hydrogen index (obtained from knowledge formation temperature and pressure, and the known equation of state of natural gas) and the actual porosity (generally obtained from other well logs) connects apparent NMR gas-filled porosity with gas saturation.

Hydrogen index is therefore a very important petrophysical parameter measurement as it is necessary for obtaining gas volumes. In the case of bulk natural gas (e.g. as found in conventional reservoirs) the Hydrogen index is easy to calculate if the pressure and temperature and gas composition are known. But for gas in shales or other tight rocks where the gas exists in free and adsorbed form determining the hydrogen index is more challenging. This is because the Hydrogen index of the adsorbed gas would be higher than the gas in the pore interiors and its dependence on pressure and temperature is difficult to accurately quantify. The free and adsorbed gas phases are also in exchange with each other. Therefore given the challenge and importance of determining the hydrogen index we discuss a few methods of determining the gas hydrogen index.

1. The HI can be determined in the lab under the same conditions as found downhole and then applied for log interpretation or for lab experiments. One methodology is the calculation of the hydrogen index from the $T_2$ distributions of the completely water-saturated and gas-saturated samples, under the conditions that the same pore spaces are occupied by either phase during their respective measurements. As the hydrogen index of water is known simply comparing the gas and water NMR T2 distributions, the HI of gas can be determined. For obtaining the hydrogen index at specific downhole conditions, the gas phase NMR experiments have to be carried out at those same conditions. Instead of water, other solvents (e.g. toluene) which are better in saturating the gas shales can also be used.

The results of one such experiment are summarized in Table 1. Note that the calculated HI is the weighted average across all pores in the sample. The calculated HI are substantially higher than that of bulk methane at 5 kpsi and 30° C. (HI~0.42) in this case. The average HI of the 4 samples in this particular example is 0.735, and is higher than the HI of bulk methane at the same pressure and temperature.

TABLE 1

The HI results of the 4 gas shale core samples.

| Gas Shale Sample | Hydrogen index (HI) |
|---|---|
| Sample #1 | 0.71 |
| Sample #2 | 0.86 |
| Sample #3 | 0.73 |
| Sample #4 | 0.64 |

2. The hydrogen index can be calculated by comparing gas filled NMR signals (at conditions similar to those downhole) of dried cores or cuttings with porosity. As the samples are dry the only fluid is the injected gas which completely saturates the sample and thus the hydrogen index is determined as shown in eqn 12. The methods of conventional determination of porosity include but are not limited to commercially available laboratory techniques/instruments like GeoPyc and AccuPyc.

3. The hydrogen index is even more accurately calculated by carrying out the experiment detailed above for samples in their irreducible state. These experiments can be carried out on both cores and cuttings. The irreducible state can be obtained by either using well preserved cores or by creating them in the lab by saturation and centrifuging. The total porosity is the sum of the gas filled and water filled porosities. The water filled porosity can be calculated first by NMR experiments of the preserved samples or in the samples where the irreducible state is created. The gas filled remaining porosity of these samples in the irreducible state is then measured by other techniques (e.g. using pycnometer). This gas filled porosity is then compared to the NMR gas filled $T_2$ distribution (after the water contributions are subtracted) and the hydrogen index is determined.

4. The above mentioned experiments for the determination of the hydrogen index can also be carried out on drill cuttings. Just as in core samples the drill cutting samples can be measured for the NMR response of the irreducible state. The gas can then be pushed in at conditions similar to downhole and the gas phase NMR experiments carried out on them either in a laboratory or at the wellsite. The NMR of the irreducible water and gas phase can be compared to independently obtained porosity and thus the HI determined.

5. Methods like dielectric are capable of measuring the water saturations and volumes. When combined with traditional porosity measurements and gas phase NMR they can help provide the hydrogen index.

6. Creation of a HI versus pressure chart: the hydrogen index measured in the lab has to be under the same conditions (temperature, pressure, etc.) as downhole. The experiments have to be also carried out for samples from each depth as due to the pore size distributions, geometries and type the free and adsorbed gas fractions might differ and so will the hydrogen index and its dependence on pressure and temperature. But in cases where there is no drastic change in the pore seizes and type the hydrogen index can be determined for one sample for various temperatures and pressures and this chart could be used for the entire well.

Some embodiments may benefit from the following procedure. The laboratory methods show higher hydrogen index (due to higher density) than the known low HI for the gas in bulk state at the same conditions. For example, in our lab experiments on 4 different gas shale plugs the Hydrogen index measured for the gas in the kerogen are 0.71, 0.86, 0.73 and 0.64 at 5000 psi and 30° C. Thus determination and application of the hydrogen index for NMR and other petrophysical measurements can be carried out. The methods and applications include the following.

1. Gas phase NMR and comparison with water or solvent saturated NMR.
2. Gas phase NMR of dry core and cuttings and its comparison with porosity.
3. Gas phase NMR and porosity determined on samples in irreducible water saturations.
4. Carrying out all the above mentioned experiments on drill cuttings.
5. Determine water saturations from other techniques like dielectric and then along with total porosity obtaining the HI from the NMR data.
6. Creation of a HI chart.

Methods to separate the water and gas contributions:
a. NMR (1D or 2D methods like DT2, T1T2 or from T1 and T2) can be used.
b. Spectral deconvolution can be sued to aid the process.
c. dielectric,
d. resistivity
e. Cutting and core analysis are additional techniques for such applications.
f. Either in combination or by themselves.

Obtaining the Natural Gas Composition:
As proton NMR responds to only the hydrogen atoms in the gas, we need the accurate gas composition for the proper application and interpretation of the laboratory and downhole NMR measurements. Dry natural gas is mostly methane, but for wet gas the correct gas compositional analysis is important. A few ways of determining the compositional information include:

1. Mud Logging: While a well is being drilled, the drilling mud is monitored continuously for gases released. Gases are measured quantitatively by gas chromatography or other means, and associated with a particular depth interval by standard means. One example is Fluid Logging and Analysis in Real Time (FLAIR) offered by GeoServices which is owned by and commercially available from Schlumberger Technology Corporation of Sugar Land, Tex. FLAIR provides a quantitative analysis of $C_1$-$C_5$ and qualitative information on the $C_6$-$C_8$ components and light aromatics. As only lower carbon numbers are important for obtaining of gas composition, this is ideal for such analysis.

a. DFA (Downhole Fluid Analysis): DFA is used for characterizing the distribution of reservoir-fluid properties downhole. The DFA technique is based largely on optical spectroscopy and provides hydrocarbon composition in five groups: methane ($C_1$), ethane ($C_2$), propane to pentane ($C_3$-$C_5$), hexane and heavier hydrocarbons ($C_{6+}$), and carbon dioxide ($CO_2$).

b. Standard fluid analysis: Laboratory fluid analysis of the released gas or from production data or information/analysis in offset wells.

Some embodiments may benefit from the following methods for obtaining the natural gas composition. As proton NMR responds to only the hydrogen atoms in the gas we need the accurate gas composition for the lab experiments explained above. Dry natural gas is mostly methane, but for wet gas the correct gas compositional analysis is important. A few ways of determining the compositional information include:

a. Mud logging.
b. DFA.
c. Standard fluid analysis.
d. Production data or from offset wells.

Applications of the Hydrogen Index:
The multi fluid, multi mineral inversion models like the Schlumberger standard ELAN models are based on density of the formation fluids and the matrix. ELAN is a non-deterministic petrophysical analysis package available from Schlumberger Technology Corporation of Sugar Land, Tex. The density of the gas phase is thus an important parameter for interpreting various downhole logs. Once the hydrogen index of the gas phase is obtained it can be converted into a gas phase density and can be used for the various other petrophysical measurement interpretation. Some embodiments may benefit from applications of the hydrogen index such as petrophysical applications which include but are not limited to a. Density logging: The hydrogen index determined form the lab experiments can be converted into a density and used for density log interpretation.

b. Neutron logging: The hydrogen index determined from the above mentioned NMR lab experiments can be directly used for neutron log interpretation.

Some examples other than NMR include:
Neutron Logs:
Neutron tools are sensitive to the formation hydrogen index as they respond strongly to neutron scatterers. Protons are good neutron scatterers, so in general the neutron tools are sensitive to the protons—ie. the hydrogen index. Therefore determining the hydrogen index from the above mentioned NMR experiments we can directly apply them to the neutron logs for their petrophysical evaluation.

Density Measurements:

The density log responds to the electron density of the formations. The electron density depends on the bulk density of the formation which depends on the density of the rock matrix material, the density of the formation fluids and porosity. Thus the actual density of the gas in the unconventional reservoirs at downhole conditions in an important input. Normally this is known for bulk gas if the temperature and pressure and gas compositions are known. But for unconventional plays they can be obtained from the hydrogen index, which is in turn determined using the NMR based measurements detailed above.

Correlation of NMR Relaxation Distributions with Material Properties:

The absolute value of the gas relaxation times can be correlated to the lithology (Organic kerogen or carbonate content etc) in laboratory experiments or from logs as shown in FIG. 10. Therefore this correlation can be used to determine the lithology from NMR relaxation logs or core data or vice versa. The $T_2$ distributions can also be sued to obtain the surface to volume ratios and thus the pore size distributions once the surface relaxivity of the shales are determined. The volume of gas determined from the NMR gas logs can be correlated to the TOC and thus can be used to provide an NMR derived TOC log.

Overlapping Gas and Water Signals

NMR logs downhole might have overlapping water and gas signals. If the water contribution is separated then the gas volumes can be calculated using the gas hydrogen index. To separate the water contribution a number of techniques can be used. Some of them include 1. NMR Measurements:

If the gas and water contributions can be separated in the $T_2$ dimension then the gas saturation factor ($S_g=1-S_w$) can be calculated. But in magnetic resonance $T_2$ logs, water and gas signals from gas shale will often overlap and thus $\phi_{MR}$(water) cannot be easily determined. This has been shown to be true even though the irreducible water magnetic relaxation time peaks at 1 ms and gas magnetic relaxation time peaks at 10 ms. Even if the water and gas signals are resolvable in laboratory $T_2$ measurements, this can be a challenge downhole because of the low signal-to-noise ratio due to low porosity of gas shale reservoirs (Kausik et al., 2011). Other NMR measurements like D-$T_2$ and $T_1$-$T_2$ experiments maybe used for the separation of the water and gas contributions.

NMR D-$T_2$ measurements can be applied for the better resolution of the water and gas signals, especially in situations where there is significant overlap in the relaxation dimension. As an example, D-$T_2$ experiments on Vycor porous glass (4 nm narrow pore size distribution) is shown. Note that the gas and water $T_2$ distributions overlap and thus cannot be separated in the relaxation dimension. Though both water and gas have lower diffusion coefficients compared to their respective bulk values due to restricted diffusion, they are well separable in the diffusion dimension (Kausik et al., 2011). The oil if present would also be clearly be differentiated from the other contributions by falling on the alkane line.

NMR $T_1$-$T_2$ correlation experiments can also be carried out for the separation of the irreducible water and confined gas components. This is based on the premise that the $T_1/T_2$ ratio of the irreducible water is different from that of the confined gas and thus cutoffs in both the dimensions would help in their better separation.

Spectral deconvolution: Spectral deconvolution techniques can be applied to separate the gas and water contributions from the various $T_2$, $D_r$-$T_2$ and $T_1$-$T_2$ experiments.

2. Resistivity Measurements:

In clean sands, applying resistivity measurements is fairly straightforward, but source rocks are challenging. A number of models exist for determining the water saturations especially in shaly sand. These can be broadly separated to those approaches based on V-Shale (resistivity models) or Cation exchange (conductivity models). Some of these models (eg. Simandoux model and Modified Simandoux model) have been applied successfully for the determination of water volumes in gas shale and other unconventional reservoirs.

3. Dielectric Measurements:

Dielectric logs are another method to obtain the water volumes. The dielectric constant method has been tested in oil shales. It has been found to give reliable results for water saturation in the presence of clays, various other minerals, and kerogen. Inorganic minerals, kerogen, and gas all have low permittivity, see and thus they all appear to be part of the "matrix" (grain space), in contrast to water, which has a very high permittivity. Gas response can then be determined using $$\phi_{MR}(gas)=\phi_{MR}-\phi_{diel}(water) \quad (13)$$

where $\phi_{MR}$ is a total magnetic resonance porosity (e.g. TCMR) and $\phi$diel(water) is the water-filled porosity as determined by a dielectric logging tool. Some of the challenges with the dielectric response include those of OBM (Oil Based Mud) and the presence of clays. Just as in the case of resistivity, existing and newly developed models can be applied to interpret the dielectric data for water saturation in gas shale.

4. Cuttings Analysis:

During drilling process, rock debris is carried up from the bottom of the well to the surface by the recirculation of the drilling fluid. Such debris also called cuttings are inspected at the well site by geologists and petrophysicists to determine drilling process and estimate rock properties like composition and microstructure as a function of drilling depth. Drill cuttings are inspected at the well site by geologists and petrophysicists to determine drilling process and estimate rock properties like composition and microstructure as a function of drilling depth. NMR experiments to determine the residual water, NMR gas phase experiments for determining gas relaxation and diffusion properties can be carried out on these samples to provide depth dependent information. Analysis (using NMR or other techniques like density, resistivity, dielectric etc) of the drill cuttings can be carried out after letting the gas out to determine the water volumes. Additional cuttings analysis techniques are provided by U.S. patent application Ser. No. 13/447,109, entitled, "Reservoir And Completion Quality Assessment In Unconventional (Shale Gas) Wells Without Logs Or Core," filed on Apr. 13, 2012, which is incorporated by reference herein.

5. Core Analysis:

Cores drilled from the formation can be preserved and examined in the lab for the estimation of the irreducible water content. If the gas could escape leaving the water behind then the NMR response of the core can be used to determine the water volume. But maintaining the core with the downhole water saturations can be challenging. Thus an alternative is to saturate the core with brine (same as the formation salinity) and then centrifuge it to the pressures to result in irreducible water saturations as expected downhole. Measuring the NMR such samples helps in the estimation of the water filled porosity. This methodology works well for unconventional plays like gas shale where the water is mainly present at irreducible state.

NMR Logging in Gas Shales

The relaxation times ($T_2$ and $T_1$) of the gas in the (nano-micrometer) pores of the gas shale have been found to be short compared to those in conventional reservoirs. Therefore the presence of gas in gas shale can be identified in the NMR logs when acquired with appropriate pulse sequences. The relaxation ($T_2$ and $T_1$) window can be determined through laboratory measurements on cores specific to the reservoir at in situ conditions. Alternatively, the relaxation ($T_2$ and $T_1$) window can be determined from the NMR response of the gas bearing zone in the NMR logs of the reservoir. For example in our lab experiments on gas shale plugs the $T_2$'s are peaked about 8-15 ms and $T_1$'s at about 20-40 ms respectively at 5000 psi and 30° C.

The relaxation times ($T_2$ and $T_1$) of the bound water in the gas shales have been identified to be very short and thus the bound fluid volume can be identified in the NMR logs when acquired with appropriate pulse sequences. The relaxation ($T_2$ and $T_1$) times for the BFV can be determined through laboratory measurements on cores/cuttings specific to the reservoir at insitu conditions and/or can be determined from the NMR response of the BFV in the NMR logs of the reservoir. For example in our lab experiments on gas shale plugs the BFV $T_2$'s are peaked about 0.5-2.5 ms.

The diffusion coefficients of the gas in gas shale plays are reduced from those in formations where the gas is in bulk state. The diffusion coefficients of the gas in gas shale can be determined through laboratory measurements on cores/cuttings specific to the reservoir at insitu conditions and/or can be determined from the NMR response of the gas in the NMR logs of the reservoir. For example in our lab experiments on gas shale plugs, the reduction is by about a factor of 5 at 5000 psi and 30° C.

The diffusion coefficients of the BFV in gas shale plays are reduced from that in formations where the water/brine exists in bulk state. The diffusion coefficients of the BFV in gas shale can be determined through laboratory measurements on cores specific to the reservoir at in situ conditions and/or can be determined from the NMR response of the BFV in the NMR logs of the reservoir.

Relaxation—Conventional NMR fluid typing modes focus on gas in the free fluid region with long $T_1$ and $T_2$ relaxation times. In gas shales, we have shown that $T_2$ has the values of few tens of milliseconds. Therefore, the NMR acquisition parameters in gas shales should focus on the shorter relaxation times. Even though it has been shown that the gas HI in gas shales is more favorable than the gas HI in conventional reservoirs, pulse sequences have to address the low SNR, inherent to low porosity. A SNR greater than 20 is recommended for NMR logging in gas shales. One way to achieve this goal is to stack repeated data obtained from pulse sequences with just long enough WT to polarize up to $T_2 \sim 100$ ms, and with high sensitivity to low $T_2$ region (0.1 ms-50 ms) by using short bursts and the smallest possible inter-echo time. Therefore NMR pulse sequences with short recycle delays to cover the short relaxation times can be carried out enabling the application of more scans for the same time as conventional logging to overcome the signal to noise ratio issue encountered in these low porosity plays.

Diffusion—The reduction in the diffusion coefficients caused by restricted diffusion in small pores and adsorption on the pore surface has been quantified by our laboratory experiments. This information can be used to determine the appropriate diffusion encoding times for the downhole NMR tools in for gas shale plays. Typically experiments can be carried out with gas phase at downhole pressure and temperature to determine the NMR logging parameters for each well or depth. This is especially important as the $T_2$'s are short in these plays and thus application of most conventional diffusion encoding times would result in the loss of signal.

Method Considerations

The relaxation properties that have been discovered enable the formulation of new 1D-$T_1$ or $T_2$ pulse sequences targeting the gas and water response in gas shale. For example, from our experiments on gas shale plugs we propose for that reservoir new pulse sequences consisting of more number of scans (~50) covering the 0-50 ms with shorter wait times of around 250 ms to focus on the gas in kerogen and BFV contributions. These help provide higher accuracy and optimum SNR (>20) for better resolution at the shorter relaxation times.

The relaxation and diffusion properties of fluids in gas shale that have been discovered enable the application of new 2D $T_1$-$T_2$ or $DT_2$ or $DT_1$ or other multi dimensional NMR pulse sequences targeting the gas and water response in gas shale. For example, these new pulse sequences would consist of more number of scans at short wait times for improved measurement of the fast relaxing components as explained earlier. In combination, the right diffusion encoding times can be chosen to better cover the gas diffusion (e.g. in core samples: $1.10^{-7}$ to $1.10^{-9}$ m$^2$/s@ 5000 psi and 30° C.) and water diffusion coefficients. Special diffusion encoding times based D-$T_2$ pulse sequences are necessary to enable optimized logging to efficiently measure the short $T_2$ contributions as the diffusion properties can be used to tune the parameters for diffusion encoded pulse sequences downhole. For example, as the gas $T_2$ is peaked at 10 ms for some of the gas shales studied the encoding times would be far shorter to avoid loss of these signals due to relaxation.

The study of the relaxation and diffusion properties of the gas in gas shale using specialized pulse sequences enable the separation of the gas in the kerogen from the gas in the large pores/fractures of the matrix.

The special laboratory relaxation and diffusion experiments devised for gas shales enable the application of field based cut-offs in both the dimensions in the $DT_2$ or $T_1T_2$ or $DT_1$ or other multidimensional NMR logs. The cutoffs can be determined through laboratory measurements on cores or cuttings specific to the reservoir at insitu conditions and/or can be determined from the NMR response of the logs of the reservoir. For example, from our lab experiments on gas shale the $T_2$ and $T_1$ cutoffs for the gas in kerogen are about 50 ms and 100 ms respectively at 5000 psi and 30° C.

1. We can interpret the lithology type, size of the pores and adsorbed gas based on the relaxation time of the gas relative to the response of bound water. For example the absolute value of the $T_2$ of the confined gas is about 100 ms for silica glass with 4 nm pores, about 8-15 ms for gas in gas shale samples. With increased adsorption and increase of small kerogen pores, the relaxation times are reduced.

2. The absolute value of the gas relaxation times can be correlated to the lithology (Organic kerogen or carbonate content etc) in laboratory experiments or from logs. Therefore this correlation can be used to determine the lithology from NMR relaxation logs or core data or vice versa.

3. The quantity of gas determined from the NMR gas logs can be correlated to the TOC and thus can be used to provide an NMR derived TOC log.

We claim:

1. A method for characterizing a subterranean formation traversed by a borehole, comprising:
    obtaining a sample of the subterranean formation;
    measuring, uphole, the porosity of the sample;
    using a nuclear magnetic resonance (NMR) tool downhole in the borehole, sending NMR pulse sequences configured for formation pore size and measuring NMR signals that characterize the formation at a location in the formation;
    analyzing the signals to find an apparent gas porosity of the formation at the location; and
    determining a hydrogen index of the subterranean formation from the apparent gas porosity and from the porosity of the sample.

2. The method of claim 1, further comprising:
    using the NMR tool at an additional location in the formation and measuring NMR signals at that additional location to characterize the formation at that additional location;
    analyzing the NMR signals at that additional location to find an apparent gas porosity of the formation at the additional location; and
    estimating a corrected gas porosity of the formation at the additional location using the hydrogen index and the apparent gas porosity of the formation at the additional location.

3. The method of claim 2, wherein the estimating comprises estimating according to $\phi_{MR(gas)} = HI_g S_g \phi$ where $HI_g$ is the hydrogen index, $\phi_{MR(gas)}$ is the apparent gas porosity of the formation at the additional location, $S_g$ is gas saturation and $\phi$ is the corrected gas porosity.

4. The method of claim 3, wherein the determining a hydrogen index comprises obtaining a plurality of samples of the subterranean formation, and measuring, uphole, the porosities of the sample under controlled temperature and pressure.

5. The method of claim 4, wherein the samples comprise core, cuttings, or a combination thereof.

6. The method of claim 1, wherein the NMR signals define relaxation times or echo decays, and an inter-echo time, and the relaxation times or echo decays are of the same order of magnitude of the inter-echo time.

7. The method of claim 1, wherein the sample comprises a core, cuttings, material in communication with a wellbore, or a combination thereof.

8. The method of claim 1, wherein the formation comprises shale, coal, kerogen, or a combination thereof.

9. The method of claim 1, wherein, the determining a hydrogen index further comprises analyzing a mud log.

10. The method of claim 1, wherein the analyzing the signals to find an apparent gas porosity of the formation at the location further comprises distinguishing a gas contribution from a liquid contribution to the signals.

11. The method of claim 1, wherein the determining a hydrogen index of the subterranean formation further comprises conducting a fluid analysis using fluid collected from the borehole.

12. The method of claim 1, further comprising conducting resistivity measurements.

13. The method of claim 1, further comprising conducting dielectric measurements.

14. A method for characterizing a subterranean formation traversed by a borehole, comprising:
    obtaining a sample of the subterranean formation;
    measuring, uphole, the porosity of the sample;
    using a nuclear magnetic resonance (NMR) tool downhole in the borehole, sending NMR pulse sequences configured for formation pore size and measuring NMR signals that characterize the formation at a location in the formation;
    analyzing the signals to find an apparent gas porosity of the formation at the location; and
    determining a hydrogen index of the subterranean formation from the apparent gas porosity and from the porosity of the sample,
    wherein the formation comprises a distribution of pore sizes of 10 nm or more.

15. The method of claim 14, further comprising:
    using the NMR tool at an additional location in the formation and measuring NMR signals at that additional location to characterize the formation at that additional location;
    analyzing the NMR signals at that additional location to find an apparent gas porosity of the formation at the additional location; and
    estimating a corrected gas porosity of the formation at the additional location using the hydrogen index and the apparent gas porosity of the formation at the additional location.

16. The method of claim 15, wherein the estimating comprises estimating according to $\phi_{MR(gas)} = HI_g S_g \phi$ where $HI_g$ is the hydrogen index, $\phi_{MR(gas)}$ is the apparent gas porosity of the formation at the additional location, $S_g$ is gas saturation and $\phi$ is the corrected gas porosity.

17. The method of claim 14, wherein the NMR signals define relaxation times or echo decays, and an inter-echo time, and the relaxation times or echo decays are of the same order of magnitude of the inter-echo time.

18. The method of claim 14, wherein the sample comprises a core, cuttings, material in communication with a wellbore, or a combination thereof.

19. The method of claim 14, wherein the formation comprises shale, coal, kerogen, or a combination thereof.

* * * * *

UNITED STATES PATENT AND TRADEMARK OFFICE
CERTIFICATE OF CORRECTION

PATENT NO. : 9,720,124 B2
APPLICATION NO. : 14/119708
DATED : August 1, 2017
INVENTOR(S) : Ravinath Kausik Kadayam Viswanathan et al.

It is certified that error appears in the above-identified patent and that said Letters Patent is hereby corrected as shown below:

On the Title Page

(75) Inventors:
Fourth Inventor's name is corrected from "Baarinadh Vissapragada" to --Badarinadh Vissapragada--.

Signed and Sealed this
Ninth Day of August, 2022

Katherine Kelly Vidal
*Director of the United States Patent and Trademark Office*